United States Patent [19]

Kalb

[11] Patent Number: 4,969,897
[45] Date of Patent: Nov. 13, 1990

[54] INTRAOCULAR LENS WITH RETRACTABLE LEG

[76] Inventor: Irvin M. Kalb, 16 Pequot Trail, Westport, Conn. 06880

[21] Appl. No.: 649,798

[22] Filed: Sep. 12, 1984

[51] Int. Cl.$^5$ .............................................. A61F 1/16
[52] U.S. Cl. ........................................................ 623/6
[58] Field of Search ........................................... 623/6

[56] References Cited

U.S. PATENT DOCUMENTS

| | | |
|---|---|---|
| 4,073,014 | 2/1978 | Poler . |
| 4,118,808 | 10/1978 | Poler . |
| 4,149,279 | 4/1979 | Poler . |
| 4,159,546 | 7/1979 | Shearing . |
| 4,192,022 | 3/1980 | LaHaye . |
| 4,280,232 | 7/1981 | Hummel . |
| 4,296,501 | 10/1981 | Kelman . |
| 4,343,050 | 8/1982 | Kelman . |
| 4,463,457 | 8/1984 | Kelman . |
| 4,477,931 | 10/1984 | Kelman . |
| 4,513,456 | 4/1985 | White . |
| 4,527,294 | 7/1985 | Heslin ................................... 623/6 |
| 4,615,701 | 10/1986 | Woods . |
| 4,666,444 | 5/1987 | Pannu . |

FOREIGN PATENT DOCUMENTS

2352537 12/1977 France .
2515956 5/1983 France .

*Primary Examiner*—V. Millin
*Attorney, Agent, or Firm*—Scully, Scott, Murphy & Presser

[57] ABSTRACT

An intraocular lens has a flexible positioning leg which is releasably held in a retracted position by cooperation between the leg and means on the lens body.

25 Claims, 8 Drawing Sheets

INTRAOCULAR LENS WITH RETRACTABLE LEG

BACKGROUND OF THE INVENTION

This invention relates to intraocular lenses, and more specifically to lenses which are placed in the posterior chamber of the eye following removal of the natural lens from the eye. Such lenses are generally inserted into the posterior chamber through an incision in the cornea. Various configurations of projections or "legs" have been proposed which extend from the lens body and press gently against the top and bottom surfaces of the posterior capsule and thereby hold the lens in the center of the capsule. Inserting lenses having such legs can be difficult because of the increasingly complex curvature of the legs, because the legs are frequently as long as or longer than the diameter of the lens, and because the legs are so small that they can be difficult to see to ensure that the lens has been inserted properly. In addition, the length of the incision which the surgeon must make in the patient's eye can be affected by the length of the legs and the distance that they extend from the lens body. There is a need for an intraocular lens which achieves the desirable characteristics of lenses having flexible centering legs but which reduces the difficulty of insertion and the length of the incision which the lens requires.

The following patents describe intraocular lenses which employ various types of flexible or retractable legs, but which do not suggest the construction of the present invention nor its ease and simplicity of operation: U.S. Pat. No. 4 343 050; U.S. Pat. No. 4 296 501; U.S. Pat. No. 4,280,232; U.S. Pat. No. 4,192,022; and U.S. Pat. No. 4,159,546.

SUMMARY OF THE INVENTION

The present invention comprises an intraocular lens for placing into the posterior chamber of an eye, comprising (a) a lens body;

(b) leg means, comprising a plurality of filament-like legs having one end attached to said lens body and a free end, for centering the lens body in the posterior chamber when each of said legs is in an unretracted position, wherein at least one of said legs is capable of moving into said unretracted position from a retracted position in which said leg is closer to the lens body than when in said unretracted position; and (c) means formed in said lens body for releasably holding said movable leg in said retracted position.

In one preferred embodiment of the invention, the movable leg springs into its unretracte position when it is released from the means (c).

In another preferred embodiment, the lens includes cooperating means on said movable leg, and the cooperating means and the means formed in the lens body for releasably holding the movable leg are configured to interlock releasably with each other, wherein when said means are interlocked said movable leg is thereby held in said retracted position.

DETAILED DESCRIPTION OF THE INVENTION

Referring first to FIGS. 1, 5, 8 and 9, the lens 1 of the present invention includes a lens body 2. Lens body 2 is usually generally circular, and is made of refractive, physiologically inert material such as polymethyl methacrylate. The lens body generally has a convex front surface and a convex or planar back surface. The lens body 2 is typically about 4 to 6 mm in diameter, and typically about 0.7 to 1.3 mm thick in the middle diminishing to a thickness of typically about 0.3 mm at the edge. Lens body 2 can include an annular ring ("haptic") 2A, seen in FIG. 1 but omitted from the lens of FIG. 5. The haptic surrounds all or part of the refractive region of the lens, but does not need to be refractive. The lens body can be cast or machined in any manner now used for conventional intraocular lenses.

The lens 1 also comprises leg means 3 for holding the lens body centered in the posterior chamber of the eye. Leg means 3 preferably comprises two legs 3A and 3B. Legs 3A and 3B are typically made of flexible physiologically insert plastic material, about 0.10 to 0.20 mm thick, such as polypropylene (a satisfactory brand of polypropylene is sold under the name "Prolene"). The legs, which need not be circular in cross-section, can be cast or machined integrally with the lens body, or can be cast separately and then attached to the lens body by inserting an end of each leg into small holes drilled in the lens body. The leg to be flexed to a retracted position (hereinafter termed leg 3A) can be provided with serrations 15, shown in FIG. 5, on its surface to facilitate flexing the leg to the degree necessary to accomplish the goals of this invention.

The invention is most readily adapted to legs of the type which are attached at one end 4 to the edge of the lens body 2 or haptic 2A, and which have at rest a generally curved shape. In a preferred embodiment, each leg is dimensioned so that the distance from the center of the lens to the leg is greatest at a point between the two ends of the leg, and the free end of the leg is closer to the center of the lens than to the end of the leg which is attached to the lens body. In this way, portions 5 of each leg can contact the top and bottom surfaces within the posterior chamber in a tangential manner. Examples of lenses whose legs can be retracted in accordance with this invention include the generally "C"-shaped legs shown in FIG. 1; the "J"-shaped legs exemplified by U.S. Pat. No. 4,159,546; and even the "S"-shaped and multi-curved legs exemplified by U.S. Pat. No. 4,418,431.

Figure 2:
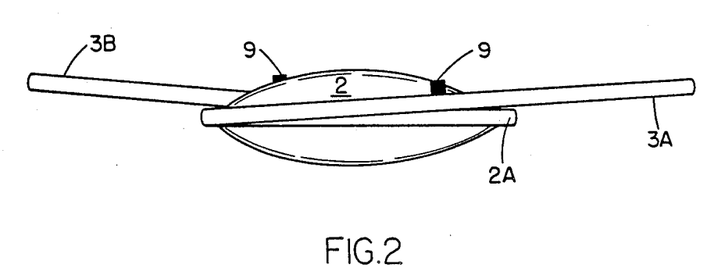
FIG. 2 is a side view of the lens of FIG. 1.

Preferably, the legs are attached to the lens body at diametrically opposite points. The legs can lie in a plane which is parallel to the plane of the lens body 2, or (see FIG. 2) each leg can lie in a plane which forms an acute angle (about 30° or less) with the plane of the lens circumference. Preferably, the legs define arcs which are either arcs of a circle whose radius is greater than that of the lens body, or arcs of an ellipse whose minor axis is greater than the radius of the lens body. The legs will generally have a length greater than a quarter of the lens body circumference, and frequently greater than half that circumference. However, the precise shape and position of the legs is not crucial provided that the legs can hold the lens centered in the wearer's eye; that at least one leg can be flexed from its rest position into a retracted position; and that the leg can be held in the retracted position by appropriate means described below.

Figure 3:
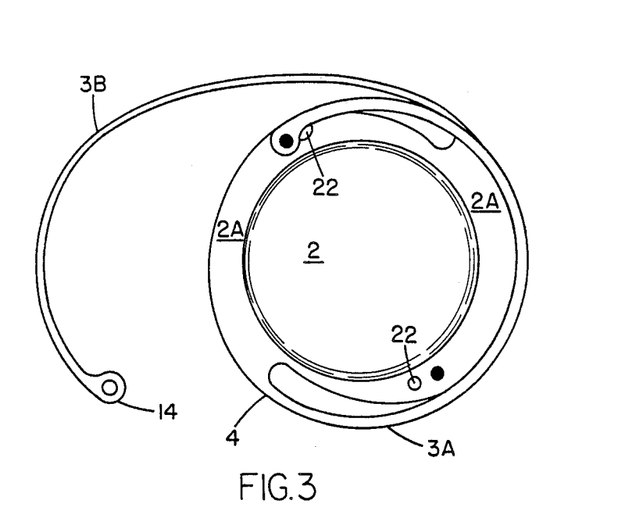
FIG. 3 is a view of the lens of FIG. 1 in the leg-retracted position.
Figure 4:
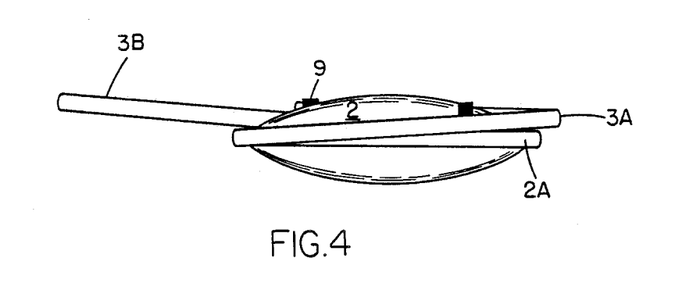
FIG. 4 is a side view of the lens of FIG. 3.
Figure 6:
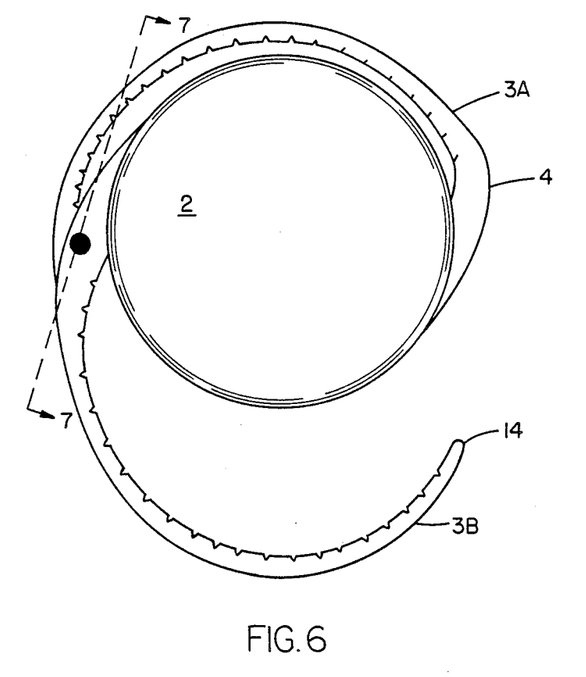
FIG. 6 is a view of the lens of FIG. 5 in the leg-retracted position.

The lens of the present invention also comprises means for releasably holding leg 3A in a retracted position. By "retracted position" is meant a position in which the area bounded by the leg and the nearest edge of the lens body is less than that area when the leg is in its rest, i.e. unretracted, position. For example, FIGS. 3 and 6 depict a leg 3A which is in a retracted position. Preferably, in the retracted position leg 3A is held alongside lens body 2, as shown in FIG. 6, or even within the circumference of the lens body, as shown in FIG. 3.

Figure 5:
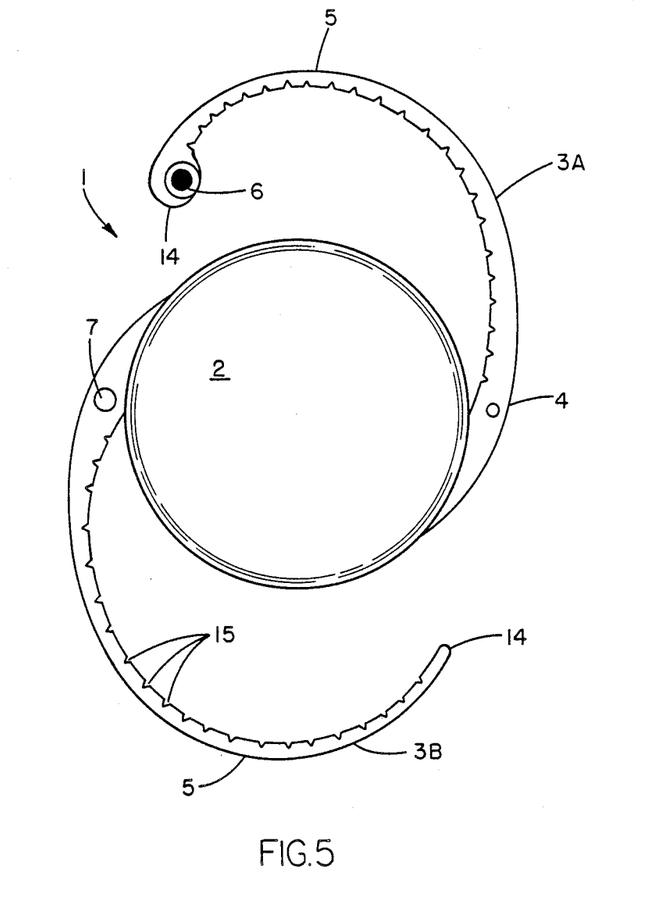
FIG. 5 is a front plan view of another embodiment of the invention.

The means for releasably holding flexed leg 3A is on the lens body, thereby avoiding any need to tie two legs to each other. By "lens body" is meant not only the part of the lens which exhibits refractive power for the patient, but also structure at the edge of the lens including the structure to which the leg is attached. In other words, the lens body is that portion of the device which remains stationary when the legs are flexed. Thus, hole 7 in FIG. 5 is considered to be on the lens body rather than on a leg. Locating the leg-holding means on the lens body protects against premature release of the leg.

The exact configuration of the means for holding the leg is not crucial, provided that the leg can be held, stay held until the surgeon desires to release it, and can be released easily by the surgeon. Many satisfactory embodiments of such means can be envisioned by the reader; examples of some are shown in the drawings.

The present invention includes embodiments in which the leg or legs which are to be held in a retracted position contain cooperating means which interlocks with the means on the lens body.

Figure 1:
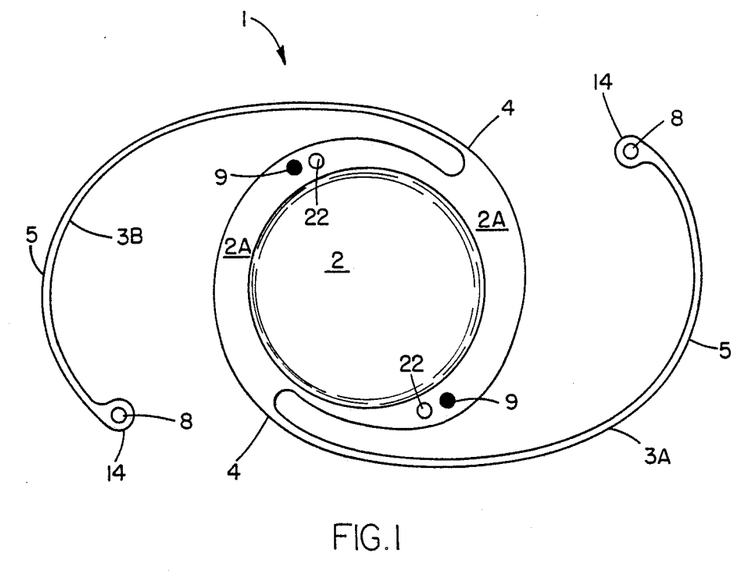
FIG. 1 is a front plan view of one embodiment of the present invention.

One acceptable embodiment is shown in FIGS. 1-4. The cooperating means on the leg 3A is a depression or hole 8. The corresponding means on the lens body is a lug 9 which fits snugly into hole 8. The lug or hole, as the case may be, that is on the lens body can be on the posterior or anterior side of the lens. FIGS. 1 and 3 also show holes 22 passing through the lens body. These holes facilitate release of the leg(s) by disengagement from the lugs.

Figure 7:
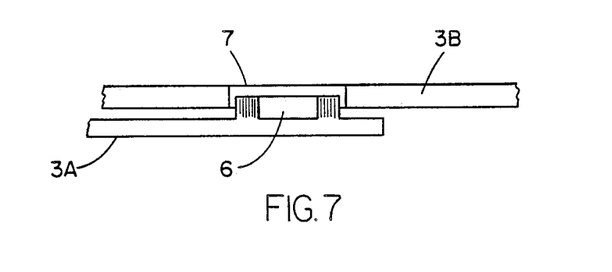
FIG. 7 is a side, cross-sectional view of the first and second cooperating means of the lens of FIG. 6, seen along the line 7—7' of FIG. 6.

In an alternative embodiment shown in FIGS. 5-7, the cooperating means on the leg comprises a raised, cylindrically-shaped lug 6, which can be hollow or solid, and the means on the lens body is a depression or hole 7 whose inside diameter is equal to or slightly larger, preferably only by up to 1-2%, than the diameter of the lug.

In other alternatives, the lug and the hole need not be circular but could be oblong, elliptical, rectangular, triangular, and so forth, so long as they cooperate as described herein. In using embodiments such as those in FIGS. 1-7, the leg 3A is forced toward the lens body until the lug overlies the hole, and then the leg and lens are pressed together slightly to engage the lug in the hole.

Figure 8:
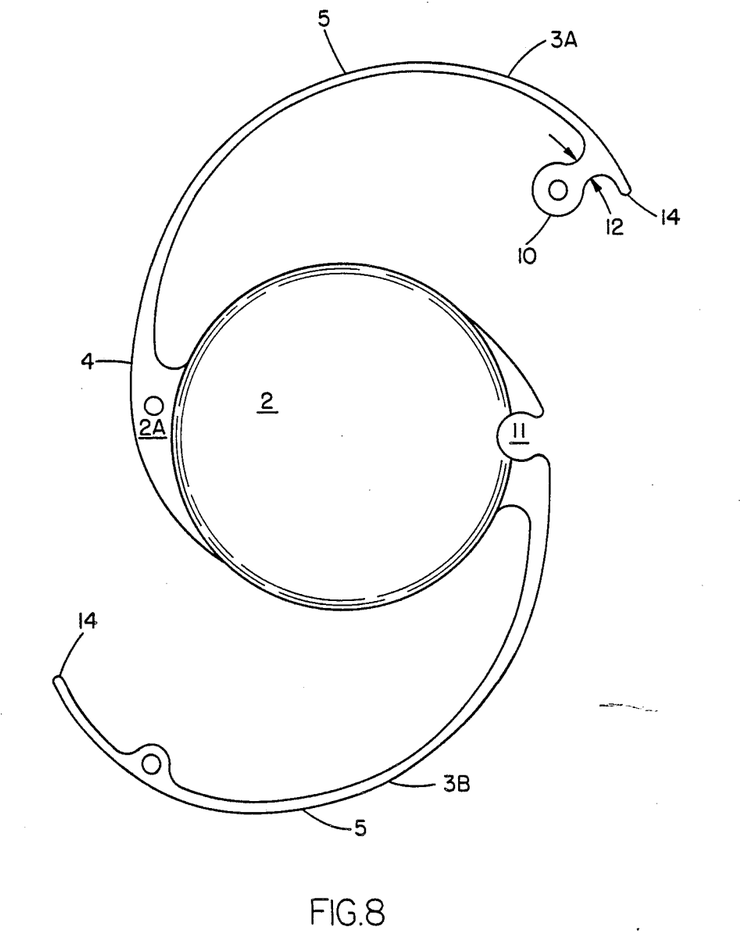
FIG. 8 is a view of another embodiment of this invention.
Figure 9:
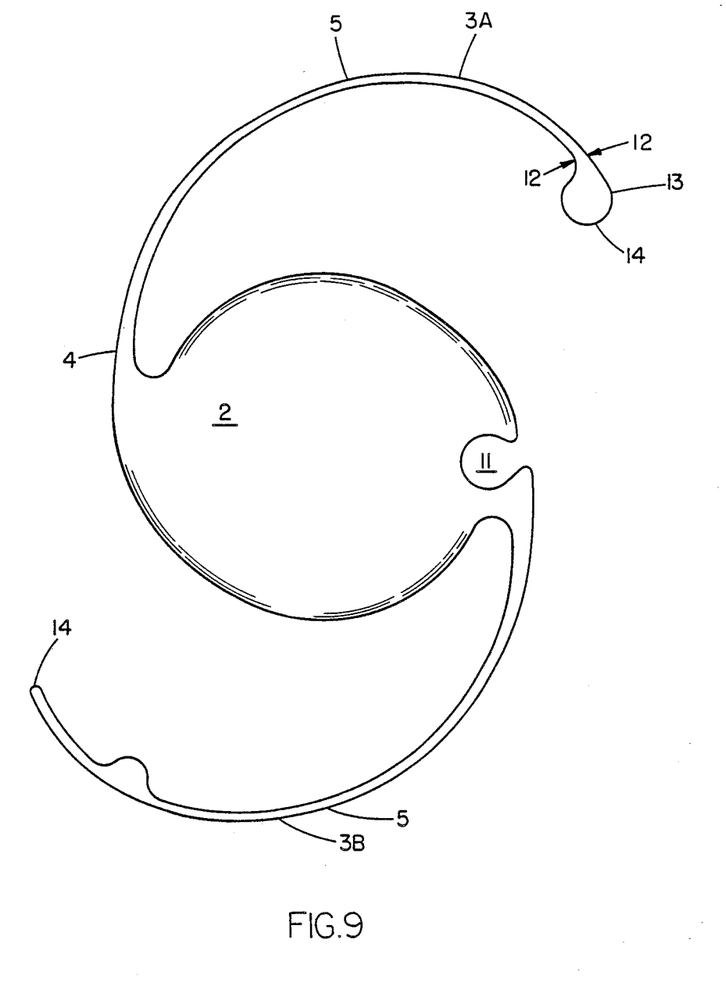
FIG. 9 is a view of another embodiment of this invention.

FIGS. 8-9 illustrate other acceptable embodiments of this invention. In FIG. 8, the cooperating means on the leg 3A comprises a lobe 10, near the end of leg 3A, which is larger in cross-section than the leg. The corresponding means on the lens body is an opening 11, formed through the edge of the lens body, which is large enough to permit lobe 10 to fit snugly into it. In this embodiment, when the leg 3A is forced toward lens body 2 and the lobe 10 is inserted into opening 11, leg 3A is in the same or approximately the same plane as lens body 2. Thus, the mouth of opening 11 preferably should be oriented so that the neck portion 12 of leg 3A which is attached to the lobe 10 can pass freely through the mouth, while the lobe itself cannot pass through the mouth.

In FIG. 9, lobe 13 is formed at the end of leg 3A, and opening 11 is formed with a size and location so that lobe 13 fits into the opening and in doing so holds leg 3A in retracted position (which is preferably as close as possible to the edge of lens body 2).

Alternatively, opening 11 of FIGS. 8-9 can be replaced by a pair of posts which extend a few millimeters from the posterior or anterior surface of the lens body, and which are generally parallel to each other and to the axis of the lens. The posts are spaced from each other a sufficient distance so that neck 12, but not lobes 10 or 13, can fit through the gap defined between the posts.

Lobes 10 and 13 can be located anywhere along leg 3A between the foot and the end 14; but the lobe, as well as lug 7 and its equivalents discussed above, is preferably located at least halfway between the foot of leg 3A and the end, and more preferably closer to the end of the leg or at the end. In this way, the risk is minimized that the free end 14 of the leg 3A can become accidentally snagged on tissue. Since lugs or posts located on the posterior surface of the lens body and dimensioned for use in this invention are generally relatively small, they do not hold the posterior capsule out of contact with the posterior surface of the lens body and do not create a space between the post and lens.

Other embodiments are possible as well. For instance, one of the cooperating means can take the shape of a hook, and the other can be a notch adapted to catch and hold the hook until the hook is dislodged.

Alternatively, the legs can be connected to a ratchet means in the lens body for gradually spreading the legs away from the lens body after it is inserted into the eye. The legs are held next to the lens body until that point by the rachet means.

Alternatively, the leg can be held in the retracted position by magnetic force between, say, a small magnet embedded in the lens body and a small piece of diamagnetic material (e.g. iron) embedded in the leg. Gentle force on the leg disengages it from the magnetic force and lets it seek its rest position.

Other embodiments of this invention do not require a cooperating means on the retracted leg.

Figure 10:
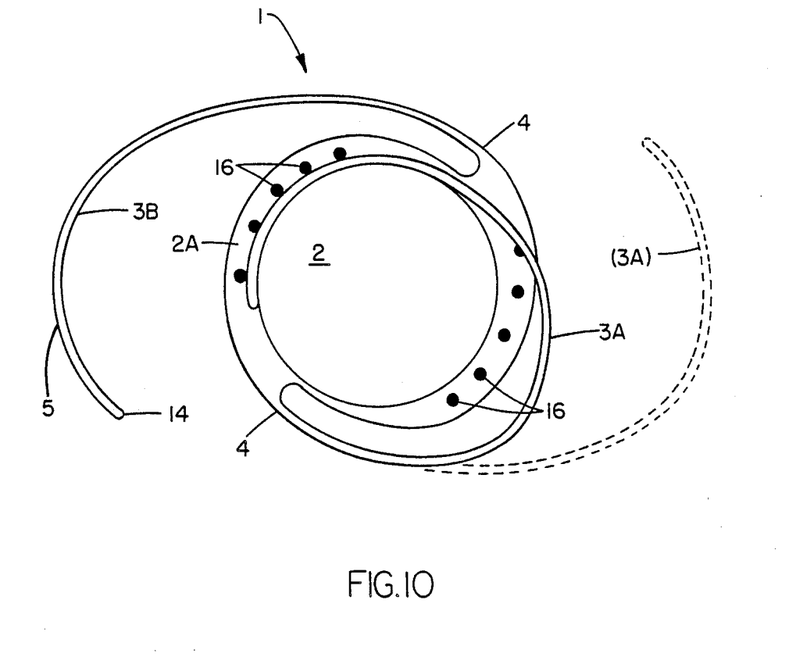
FIG. 10 is a view of another embodiment of this invention.
Figure 11:
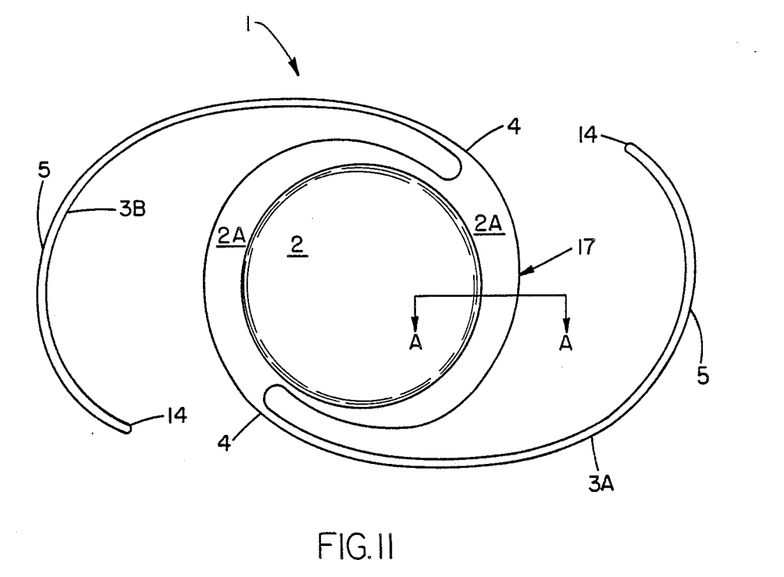
FIG. 11 is a view of another embodiment of this invention.
Figure 12:
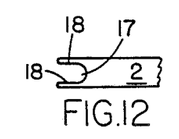
FIG. 12 is a cross-section view of one embodiment of the lens depicted in FIG. 11, seen along the line A—A of FIG. 11.
Figure 13:
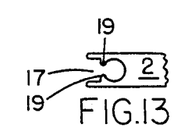
FIG. 13 is a cross-section view of one embodiment of the lens depicted in FIG. 11, seen along the line A—A of FIG. 11.
Figure 14:
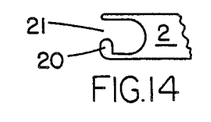
FIG. 14 is a cross-section view of one embodiment of the lens depicted in FIG. 11, seen along the line A—A of FIG. 11.

In one such embodiment, shown in FIG. 10, the means for holding the leg 3A comprises a series of posts 16 which extend parallel to the axis of the lens and which are spaced along the edge of the lens body, to restrain the leg 3A by abutment of leg 3A against the surface of the posts closer to the center of the lens. Alternatively, pairs of posts can be connected to form portions of a lip, or the portions can be connected to form a lip. As shown in FIG. 10, the leg 3A is flexed from its rest position (shown in dotted lines) so that it is held within the posts. This embodiment is advantageous in that it does not require that any special configuration of locking means be formed on the leg 3A. The posts do not need to extend beyond the surface of the lens itself.

In another embodiment, exemplified by the lens depicted in FIGS. 11–14, the means for holding the leg 3A is a groove or slot 17 formed in an annular fashion in the edge of the lens body. Leg 3A is held in groove 17 by friction with the interior walls 18 of the groove (see FIG. 12), or by frictional engagement with nibs 19 on the walls which are spaced apart within the groove (see FIG. 13). Alternatively (see FIG. 14), the groove can include a projection 20 which defines mouth 21 through which leg 3A can freely pass, and against which leg 3A is urged (in the direction of the arrow) by the compressed elastic strength of leg 3A.

To use a lens of the present invention, the surgeon prepares the lens for insertion into the eye by forcing the leg 3A toward the lens body and engaging the leg and lens body with each other. At this point, the lens will resemble those shown in FIGS. 3 and 6. Alternatively, the lens can be provided so that both legs are capable of being held by respective means in retracted positions as described above.

Then, once the patient's eye is otherwise ready to receive the intraocular lens, an incision in the eye is made which need only be long enough to accommodate the lens with leg 3A (or both legs) in the retracted position. Thus, the incision can frequently be shorter than it would otherwise have to be. The lens is inserted through the incision and through the pupil, and is positioned in the posterior chamber with an unretracted leg (if any) tangentially engaging the top or bottom surface of that chamber. Then, each retracted leg is released from the retracted position, and allowed to seek its rest position. This is done to insure a proper insertion in the "lens bag" with proper lens position next to and within the lens capsule. This releasing step is carried out by pushing or pulling lug 7, or lobes 10 or 13, out of its receiving opening, or by inserting a tool between leg 3A and lens body 2 and twisting to disengage the leg, or by an equivalent expedient which dislodges the first and second cooperating means from each other. A leg which has been retracted by means such as shown in FIGS. 1–4 can be released by inserting the end of a suitable tool through hole 22 from the side opposite the side on which the leg is, and pushing the leg to slip it free of the structure which is holding it. The reader will appreciate that if both legs are retracted, they will frequently be "folded" one over the other; freeing the one which is closer to the lens can free both legs simultaneously. The lens, with all legs freed, is then positioned within the eye.

What is claimed is:

1. An intraocular lens for placing into the posterior chamber of an eye, comprising
   (a) a lens body;
   (b) leg means, comprising a plurality of filament-like legs having one end attached to said lens body and a free end, for centering the lens body in the posterior chamber when each of said legs is in an unretracted position, wherein at least one of said legs is capable of moving into said unretracted position from a retracted position in which said leg is closer to the lens body than when in said unretracted position, and
   (c) means projecting from said lens body for releasably holding said movable leg in said retracted position.

2. A lens according to claim 1 having two of said filament-like legs.

3. A lens according to claim 1 wherein said means (c) comprises means projecting from the anterior or posterior surface of said lens body for restraining said movable leg by abutment of said leg against the side of said means closer to the center of the lens body.

4. A lens according to claim 3 wherein said restraining means comprises one or more posts.

5. A lens according to claim 1 wherein in said retracted position the movable leg lies entirely alongside or within the circumference of said lens body.

6. A lens according to claim 1 wherein said leg means comprises a pair of legs, which are attached to said lens body at diametrically opposed points, each leg being characterized in that when in its rest position its free end is closer to the center of the lens than to its own point of attachment to the lens body.

7. The lens of claim 6 wherein each of said legs defines in its rest position an arc of a circle having a radius larger than that of said lens body, or an arc of an ellipse whose minor axis is greater than the radius of said lens body.

8. The lens of claim 6 wherein said legs center the lens in the eye of the wearer by tangential contact by each leg against the tissue of the posterior capsule of the eye.

9. An intraocular lens according to claim 1 and further comprising (d) cooperating means on said movable leg, wherein said cooperating means and said means for releasably holding said movable leg are configured to interlock releasably with each other, wherein when said means are interlocked said movable leg is thereby held in said retracted position.

10. A lens according to claim 9 wherein said cooperating means is located on the half of said movable leg which is further from the point at which said leg is attached to said lens body.

11. A lens according to claim 10 wherein said cooperating means is located at the end of said movable leg.

12. A lens according to claim 9 wherein said means (c) is located on the edge of said lens body.

13. A lens according to claim 9 wherein in said retracted position the movable leg lies entirely alongside or within the circumference of said lens body.

14. A lens according to claim 9 wherein said cooperating means (d) is a cavity, and said means (c) is a lobe adapted to fit into said cavity.

15. A lens according to claim 14 wherein said cavity is a hole passing through said leg.

16. A lens according to claim 9 wherein said cooperating means (d) is a lobe having a neck portion narrower than said lobe, and said means (c) is a plurality of posts projecting from the anterior or posterior surface of said lens body, wherein said posts define therebetween a gap through which said neck, but not said lobe, can pass.

17. The lens of claim 9 wherein said means projecting from said lens body projects from the anterior surface of the lens body.

18. The lens of claim 9 wherein said means projecting from said lens body projects from the posterior surface of the lens body.

19. The lens of claim 1 wherein two of said legs are capable of moving into their unretracted positions from retracted positions in which said legs are closer to the lens body, and further comprising means projecting from said lens body for releasably holding each of said movable legs in said retracted positions.

20. The lens of claim 9 wherein two of said legs are capable of moving into their unretracted positions from retracted positions in which said legs are closer to the lens body, and further comprising means projecting from said lens body for releasably holding each of said movable legs in said retracted positions.

21. The method of correcting the vision of an eye from which the natural lens has been removed, comprising releasably holding at least one leg of a lens according to claim 1 in its retracted position by engagement of said leg with said means (c), then inserting the lens into said eye, releasing each leg held in a retracted position from its retracted position, and centering the lens within the posterior chamber of said eye.

22. An intraocular lens for placing into the posterior chamber of an eye comprising:
 (a) a lens body;
 (b) leg means, comprising a plurality of filament-like legs having one end attached to said lens body and a free end for centering the lens body in the posterior chamber when each of said legs is in an unretracted position, wherein at least one of said legs is capable of moving into said unretracted position from a retracted position in which said leg is closer to the lens body than when in said unretracted position;
 (c) first means projecting from said lens body for releasably holding said movable leg in said retractable position, wherein said first means further comprises a post projecting from the anterior or posterior surface of said lens body for restraining said movable leg by abutment of said leg against the side of said post closer to the center of the lens body; and
 (d) second means comprising a hole located on the free end of said leg means and a lug projecting from the same surface of said lens body as said first post, wherein said hole and said lug are configured to interlock releasably with each other whereby said first means and said second means are used simultaneously for restraining said movable leg in said retracted position.

23. An intraocular lens according to claim 22 wherein the free end of said leg means is S-shaped.

24. An intraocular lens for placing into the posterior chamber of an eye comprising:
 (a) a lens body;
 (b) leg means, comprising a plurality of filament-like legs having ne end attached to said lens body and a free end for centering the lens body in the posterior chamber when each of said legs is in an unretracted position, wherein at least one of said legs is capable of moving into said unretracted position from a retracted position in which said leg is closer to the lens body than when in said unretracted position;
 (c) means in said lens body for releasably holding said movable leg in said retractable position in which said means comprises a first post projecting from the anterior or posterior surface of said lens body and a second post projecting from the same surface as said first post, wherein said first post is spaced at a sufficient distance from said second post to allow a section of said movable leg closer to the end attached to said lens body to abut against a side of said first post closer to the center of said lens body and to allow a section of said movable leg closer to the free end to abut against a side of the second post farther from the center of said lens body.

25. An intraocular lens according to claim 24 wherein the free end of said leg means which comes into contact with said first post and said second post is S-shaped.

* * * * *